(12) United States Patent
Yuz (10) Patent No.: US 12,094,616 B2
(45) Date of Patent: Sep. 17, 2024

(54) AUTOMATED MATCHING IN A SECOND OPINION BROKERAGE SYSTEM

(71) Applicant: USARAD HOLDINGS, INC., Fort Lauderdale, FL (US)

(72) Inventor: Michael Yuz, Oakland Park, FL (US)

(73) Assignee: USARAD Holdings, Inc., Fort Lauderdale, FL (US)

( * ) Notice: Subject to any disclaimer, the term of this patent is extended or adjusted under 35 U.S.C. 154(b) by 191 days.

(21) Appl. No.: 17/007,497

(22) Filed: Aug. 31, 2020

(65) Prior Publication Data

US 2022/0068502 A1 Mar. 3, 2022

(51) Int. Cl.
*G16H 80/00* (2018.01)
*G06Q 50/18* (2012.01)

(52) U.S. Cl.
CPC ............ *G16H 80/00* (2018.01); *G06Q 50/18* (2013.01)

(58) Field of Classification Search
CPC ................................ G16H 80/00; G06Q 60/18
See application file for complete search history.

(56) References Cited

U.S. PATENT DOCUMENTS

| | | | |
|---|---|---|---|
| 10,997,555 B1 * | 5/2021 | Kharraz Tavakol | ... G06Q 50/22 |
| 2002/0147671 A1 | 10/2002 | Sloan et al. | |
| 2006/0026051 A1 | 2/2006 | Rose | |
| 2008/0059237 A1 | 3/2008 | Koren | |
| 2008/0275729 A1 | 11/2008 | Taggart | |
| 2009/0177405 A1 | 7/2009 | Niggerbrugg | |
| 2009/0319291 A1 | 12/2009 | Noordvyk | |
| 2010/0042653 A1 | 2/2010 | Krishnan et al. | |
| 2010/0234691 A1 | 9/2010 | Iwano | |
| 2011/0093295 A1 | 4/2011 | Mankad | |
| 2012/0065989 A1 * | 3/2012 | Massoumi | ............ G16H 40/67 |
| | | | 705/2 |
| 2012/0090043 A1 | 4/2012 | Twizere | |

(Continued)

OTHER PUBLICATIONS

Kathy Katella, Can a Second Opinion Make a Difference?, https://www.yalemedicine.org/news/second-opinions#:~:text=%E2%80%9CPatients%20should%20seek%20another%20opinion,treatment%20options%2C%E2%80%9D%20she%20says. (Year: 2020).*

(Continued)

*Primary Examiner* — Aryan E Weisenfeld
(74) *Attorney, Agent, or Firm* — Weisberg I.P. Law, P.A.

(57) ABSTRACT

A computer-implemented method includes the steps of receiving, at a processing device of a consumer computing device, consumer input indicative of consumer preferences related to the consumer request, determining, at the processing device of the consumer computing device, a set of consumer preference parameters based upon the consumer input and filtering rules, determining, at the processing device of the consumer computing device, a weighted set of consumer preference parameters based upon the consumer input and weighting rules, providing, from the processing device of the consumer computing device, the set of weighted consumer preference parameters to a processing device of a matching server, determining, at the processing device of the matching server, a list of experts that match the set of weighted consumer preference parameters, and providing, at the processing device of the matching server, the list of experts to the processing device of the consumer computing device.

4 Claims, 6 Drawing Sheets

(56) References Cited

U.S. PATENT DOCUMENTS

2012/0323593 A1  12/2012  Backhause
2013/0060579 A1   3/2013  Yu et al.
2015/0324919 A1  11/2015  Riggs et al.
2015/0356679 A1  12/2015  Schmitt
2015/0363862 A1  12/2015  Ranft et al.

OTHER PUBLICATIONS

International Search Report and Written Opinion dated Dec. 17, 2021, International Searching Authority, International Application No. PCT/US2021/048229.

* cited by examiner

AUTOMATED MATCHING IN A SECOND OPINION BROKERAGE SYSTEM

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A SEQUENCE LISTING, TABLE OR COMPUTER PROGRAM LISTING APPENDIX

Not Applicable

BACKGROUND OF THE INVENTION

1. Field of the Invention

The present invention relates generally to systems and methods for providing second opinions. In particular, examples of the present invention are related to automated consumer-expert matching in a second opinion brokerage system.

2. State of the Prior Art

A second opinion is an opinion received from a consultation with an expert other than the one a consumer originally consulted with in order to get an opinion from a differing point of view. The second opinion can be the opinion of a professional such as a medical doctor or lawyer or of a lay expert such as an auto mechanic. There are many circumstances in which it is desirable for a consumer to have a second opinion such as when the consumer is a patient and needs a medical second opinion or when the consumer is in need of a legal second opinion.

The knowledge base of not only professional experts but also of lay experts has dramatically expanded in virtually all fields with the continuing development of new technologies, equipment and increases in computing power and Internet speed. This development has made increasing amounts of information accessible to both professional and lay experts who in turn are accessible to consumers of all types by virtue of the computing devices used by such consumers. In addition, keeping up with technological and scientific advances presents challenges to all experts. Experts who are subspecialists in their fields have emerged in response to these developments and challenges. For example, a doctor who is also a radiologist may be a specialist, a bone radiologist a subspecialist, and a foot radiologist a superspecialist.

While many experts are competent in their field of expertise, skills, training and opinions vary. Experts, including physicians, have different personalities, different experiences and different training. Some experts are more conservative and others are more aggressive. Further, experts, being human beings, make mistakes. Studies have reported that mistake rates for experts can be 30% and higher. A second opinion from another expert can provide a consumer with insurance against these odds.

In medicine, the second opinion is often an important factor considered by a patient deciding on an ideal course of treatment. The opinion of a second physician can help avoid problems such as misdiagnosis, as well as give the patient peace of mind in knowing that a recommended procedure is the best course of treatment and is agreed upon by more than one professional. A second opinion also empowers a patient to make informed decisions in selecting their health care provider and where they receive their health care.

There are many reasons for a patient to seek a medical second opinion. Medical second opinions can be sought by a patient under circumstances including: 1) when a physician recommends surgery; 2) when a physician diagnoses the patient with a serious illness (such as cancer) that the patient does not believe he has; 3) when a physician recommends a treatment for the patient other than what the patient believes is necessary; 4) when the physician recommends elective surgery and a second opinion is required by an insurance policy; 5) when the patient believes that they have a condition that the physician fails to diagnose; and 6) when the physician recommends the second opinion.

Patients with access to the Internet can seek a second opinion from medical professionals located miles or even continents away. For example, telemedicine services provide a means by which doctors can consult with each other while telehealth services enable healthcare providers to remotely connect with patients. These services include consultations using online chat facilities, video conferencing, digital examination devices and clear voice conversations. Telemedicine products using the latest medical technology, including examination cameras, peripherals, scopes, remote vital sign monitors and fully-equipped telemedicine carts can be used to enhance second medical opinions. Patients can contact a physician or subspecialist directly. Or a primary care physician can facilitate a consultation with a physician or subspecialist on the patient's behalf by recommending a qualified physician or subspecialist.

The obvious value of the availability of a remote second opinion is that location is no longer a factor in the availability of a specific specialist's expertise. For example, telemedicine allows patients to connect with the ideal physician for their condition, regardless of geographic restrictions. Further, the availability of a remote second opinion can provide the consumer with a much larger pool of experts from which to choose from and the ability to select an expert that meets the consumer's specific requirements and preferences.

BRIEF SUMMARY OF INVENTION

In accordance with embodiments of the present disclosure, an automated matching system in a second opinion brokerage system provides for the virtualization of second opinion brokerage services including matching a consumer with an expert via a transparent, secure, and on-demand web portal.

In accordance with embodiments of the present disclosure, the automated matching system can include a web-based portal that enables consumers and experts to communicate with each other and with a matching server over a network. The communication can include sending a request from a consumer computing device to the matching server requesting a second opinion from an expert. As used herein, the term "computing device" can refer to mobile computing devices, such as mobile telephones, smartphones, laptop computers, and tablet computers, and stationary computing devices. The request can be represented as a set of weighted consumer preference parameters determined by the consumer computing device and related to consumer preferences including the type of second opinion requested, the subject matter of the second opinion requested, the location of the consumer, the consumer's preferred manner of consulting with the expert, the urgency of the consumer's request and desired expert characteristics. The consumer computing device can send the set of weighted consumer preference parameters to the matching server that matches the weighted consumer preference parameters with parameterized expert data to provide a list of experts matching the consumer's request. The matching server can send the list of matched experts to the consumer's computing device to be displayed to the consumer.

In some embodiments of the present disclosure, the second opinion rendered during the consultation can be a lay opinion received from a consumer consultation with a lay expert. In other embodiments of the present disclosure, the second opinion can be an expert opinion received from a consumer consultation with a professional expert. For example, the second opinion can be a medical second opinion received from a patient consultation with a medical doctor. In yet other embodiments of the present disclosure, the second opinion can be an expert opinion received from a professional consultation with another professional. In some other embodiments, the second opinion can be an opinion generated by a brokerage server in response to a request from the consumer. For example, the brokerage server can employ artificial intelligence to build a database of opinions indexed to particular consumer requests.

BRIEF DESCRIPTION OF THE DRAWING FIGURES

Non-limiting and non-exhaustive embodiments of the present invention are described with reference to the following figures, wherein like reference numerals refer to like parts throughout the various views unless otherwise specified.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help improve the understanding of various embodiments of the present disclosure. Also, common but well-known elements that are useful or necessary in a commercially feasible embodiment are often not depicted in order to facilitate a less obstructed view of these various embodiments of the present disclosure.

DETAILED DESCRIPTION OF A PREFERRED EMBODIMENT

In the following description, numerous specific details are set forth in order to provide a thorough understanding of the present disclosure. It will be apparent, however, to one having ordinary skill in the art that the specific detail need not be employed to practice the present invention. In other instances, well-known materials or methods have not been described in detail in order to avoid obscuring the present disclosure.

Reference throughout this specification to "one embodiment", "an embodiment", "one example", or "an example" means that a particular feature, structure or characteristic described in connection with the embodiment or example is included in at least one embodiment of the present disclosure. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

Embodiments in accordance with the present disclosure may be embodied as an apparatus, method, or computer program product. Accordingly, the present invention may take the form of an entirely hardware embodiment, an entirely software embodiment (including firmware, resident software, resident applications, micro-code, etc.), or an embodiment combining software and hardware aspects that may all generally be referred to herein as a "module" or "system." Furthermore, the present invention may take the form of a computer program product embodied in any tangible medium of expression having computer-usable program code embodied in the medium.

Any combination of one or more computer-usable or computer-readable media may be utilized. For example, a computer-readable medium may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present disclosure may be written in any combination of one or more programming languages.

Embodiments may also be implemented in cloud computing environments. In this description and the following claims, "cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

Figure 1:
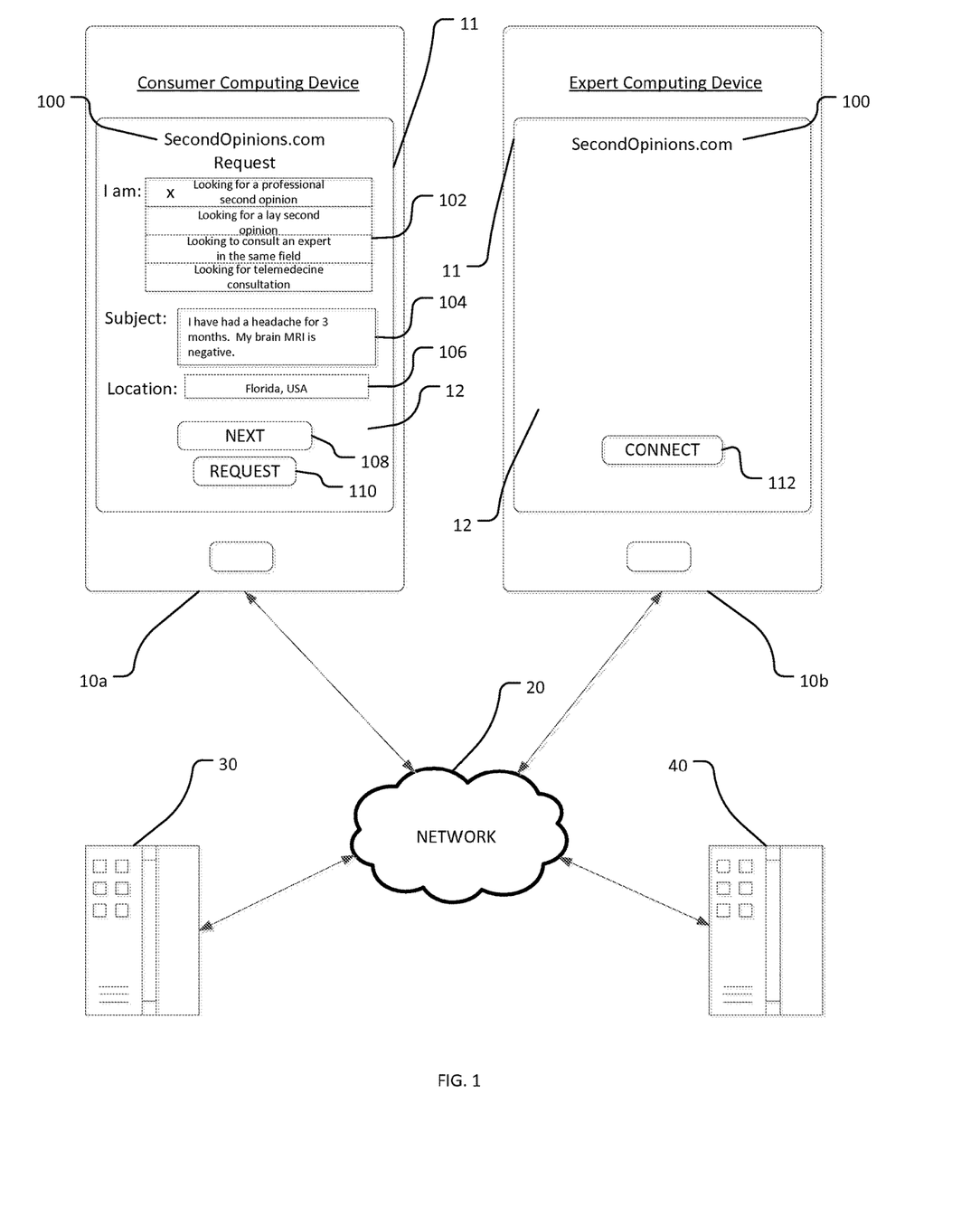
FIGS. 1-3 are schematics illustrating a consumer computing device and an expert computing device each displaying a graphical user interface in communication with a matching server in accordance with some embodiments of the present disclosure.

Referring now to FIG. 1, computing devices 10*a* and 10*b* in communication with a matching server 30 via a network 20 are illustrated. Computing device 10*a* can be a computing device used by a consumer while computing device 10*b* can be a computing device used by an expert. While one matching server 30 is illustrated, the term "matching server"

refers to one or more servers that operate in an individual or distributed manner. Further, as used herein, the term "network" can refer to any communication network including, but not limited to, a wireless network, a cellular network, an intranet, the Internet, or combinations thereof.

In the illustrated example, the computing devices 10a and 10b are displaying a graphical user interface (GUI) 12 on a touch screen 11 of the computing devices 10a and 10b. While a touch screen 11 is illustrated, it should be appreciated that other user interfaces can be used to allow the consumer and the expert to interact with their respective computing devices 10a and 10b. For example, in some embodiments of the present disclosure the user interface may employ voice recognition techniques to accept consumer and expert user input.

A third party server 40 is also illustrated. The third party server 40 can be a telemedicine or telehealth server.

In one embodiment, the GUI 12 of the consumer computing device 10a allows the consumer to request a second opinion from an expert. From a SecondOpinions.com application run by the computing device 10a and represented by the icon 100, the GUI 12 can display a menu 102 from which the consumer can select from a plurality of categories identifying the type of second opinion he is requesting. Exemplary categories include the consumer-selected "Looking for a professional second opinion", and "Looking for a lay second opinion", "Looking to consult an expert in the same field", and "Looking for a telemedicine consultation". The GUI 12 can also display a field 104 that allows the consumer to input a description identifying the subject matter of the second opinion being requested. The GUI 12 can further display a field 106 that allows the consumer to input a description identifying his location. Fields 104 and 106 provide the consumer with means for defining and inputting any of a word, phrase or sentence, or any combination thereof that describe the subject matter of his request and his location. An exemplary description of the subject matter of the consumer's request includes the illustrated sentences "I have had a headache for 3 months. My brain MRI is negative."

In some embodiments, the consumer computing device 10a is operable to analyze the consumer input and to parameterize the consumer's preferences. The consumer computing device 10a can determine consumer preference parameters by applying parsing and filtering rules to the consumer input. In some embodiments, a set of parameterized consumer preferences can include the type and subject matter of the second opinion requested by the consumer and the consumer's location. For example, the type of second opinion requested can be represented by a first consumer preference parameter "Type" and the subject matter of the second opinion requested can be represented by a second consumer preference parameter "Subject Matter". The location of the consumer can be represented by a third consumer preference parameter "Location". The computing device 10a can use the consumer input of the menu 102 and the words, phrases and sentences input by the consumer in the fields 104 and 106 to determine the type and subject matter of the second opinion requested and the consumer's location. By way of example, the computing device 10a can determine the "Type" consumer preference parameter from the consumer input in the menu 100 to be "Professional" and determine the "Subject Matter" consumer preference parameter by parsing the consumer input in the field 102 to be "Neurologic radiology". The consumer's location can be determined to be "Florida, USA".

In some embodiments, the computing device 10a can present menus and/or fields to the consumer that prompt the consumer to provide additional information related to the second opinion requested. By selecting a NEXT button 108, and with reference to FIG. 2, a menu 114 can be displayed by the GUI 12 that prompts the consumer to select his preferred type of communication with the expert. Displayed options include "Telephonic", "Online Chat", "Online Video" and "Written Report". A menu 116 can be displayed by the GUI 12 that prompts the consumer to select the urgency of his request. Displayed options include "Very urgent", "Urgent" and "Not urgent". From the consumer input of menu 114 the computing device 10a can determine a fourth consumer preference parameter "Communication Preference" and from the consumer input of menu 116 the computing device 10a can determine a fifth consumer preference parameter "Urgency".

In some embodiments, the computing device 10a can present menus and/or fields to the consumer that prompt the consumer to provide information including personal preferences and characteristics related to the requested expert. A Next button 108 can be selected by the consumer for this purpose. The computing device 10a can serve the menus and/or fields to the consumer based upon filtering rules having the determined "Type", "Subject Matter" and "Location" consumer preference parameters as operands. From the example illustrated in FIG. 1 and FIG. 2, menus and/or fields relevant to the field of neurologic radiology in the U.S. can be displayed to the consumer as illustrated in FIG. 3.

A field 120 can be displayed by the GUI 12 that prompts the consumer to input whether he has radiological images that relate to this request. Fields 122-134 prompt the consumer to select and input information related to his preferences as to the expert's specialty, sub-specialty, qualifications, certifications, number of years of experience, sex, and languages spoken, respectively. Fields 120-134 provide the consumer with a means for inputting any of a word, phrase or sentence, or any combination thereof. Based on the consumer input in fields 120-134, the computing device 10a can parse the input and determine consumer preference parameters including an "Images Available" parameter, a "Specialty" parameter, a "Sub-specialty" parameter, a "Qualifications" parameter, a "Certifications" parameter, a "No. of Yrs. Experience" parameter, a "Sex" parameter and a "Languages Spoken" parameter. The consumer computing device 10a can display additional fields in the GUI 12 based upon the determined consumer preference parameters. The consumer computing device 10a can display fields relating to the customer's ranking of his selections and input.

In some embodiments, the consumer computing device 10a can determine the "Location" consumer preference parameter from a computing device GPS navigation system.

In some embodiments, the consumer computing device 10a can assign a weight to the consumer preference parameters. If the set of consumer preference parameters are represented by the set $(c_{p1}, c_{p2}, c_{p3} \ldots c_{pn})$, where $c_{p1}$ represents the first customer preference parameter, then the set $\{w_1 c_{p1}, w_2 c_{p2}, w_3 c_{p3} \ldots W_n$ pn) where $w_1 + W_2 + W_3 + \ldots W_n = 1$ can represent a weighted set of consumer preference parameters. The consumer computing device 10a can implement weighting rules that assign weights to the consumer preference parameters. The weighting rules can include customer preference weighting rules based on the customer's ranking of his selections and input. In some embodiments, the weighting rules may including a ranking system that assigns a greater weight to the "Subject Matter" parameter than to the "Languages Spoken" parameter for example.

In one embodiment, the GUI 12 of the computing device 10a provides a means for the consumer to send the request for a second opinion from an expert to the matching server 30. A Request button 110 shown in each of GUI's 12 of the consumer computing device 10a of FIG. 1, FIG. 2 and FIG. 3 can be selected by the consumer for this purpose. When the consumer presses the Request button 110, the computing device 10a can transmit the request to the matching server 30 via the network 20. The request can include the set of weighted consumer preference parameters.

The matching server 30 can receive the request from the consumer computing device 10a and determine the "Location" consumer preference parameter from the IP address of the consumer computing device 10a if the "Location" parameter of the transmitted set of weighted consumer preference parameters is empty.

The matching server 30 can then query a database of parameterized expert data including expert characteristics, match the consumer's request with an expert and generate a list of suggested expert or experts. In some embodiments, the matching server 30 can use the consumer preference parameter having the greatest weight to query the database. In other embodiments, the matching server 30 can use a subset of the set of weighted consumer preference parameters to query the database. The matching server 30 can then transmit the list of experts back to the computing device 10a.

Upon receiving the list of experts from the matching server 30, the computing device 10a can display the list of experts in the GUI 12, thereby allowing the consumer to select an expert from the list of experts.

Figure 2:
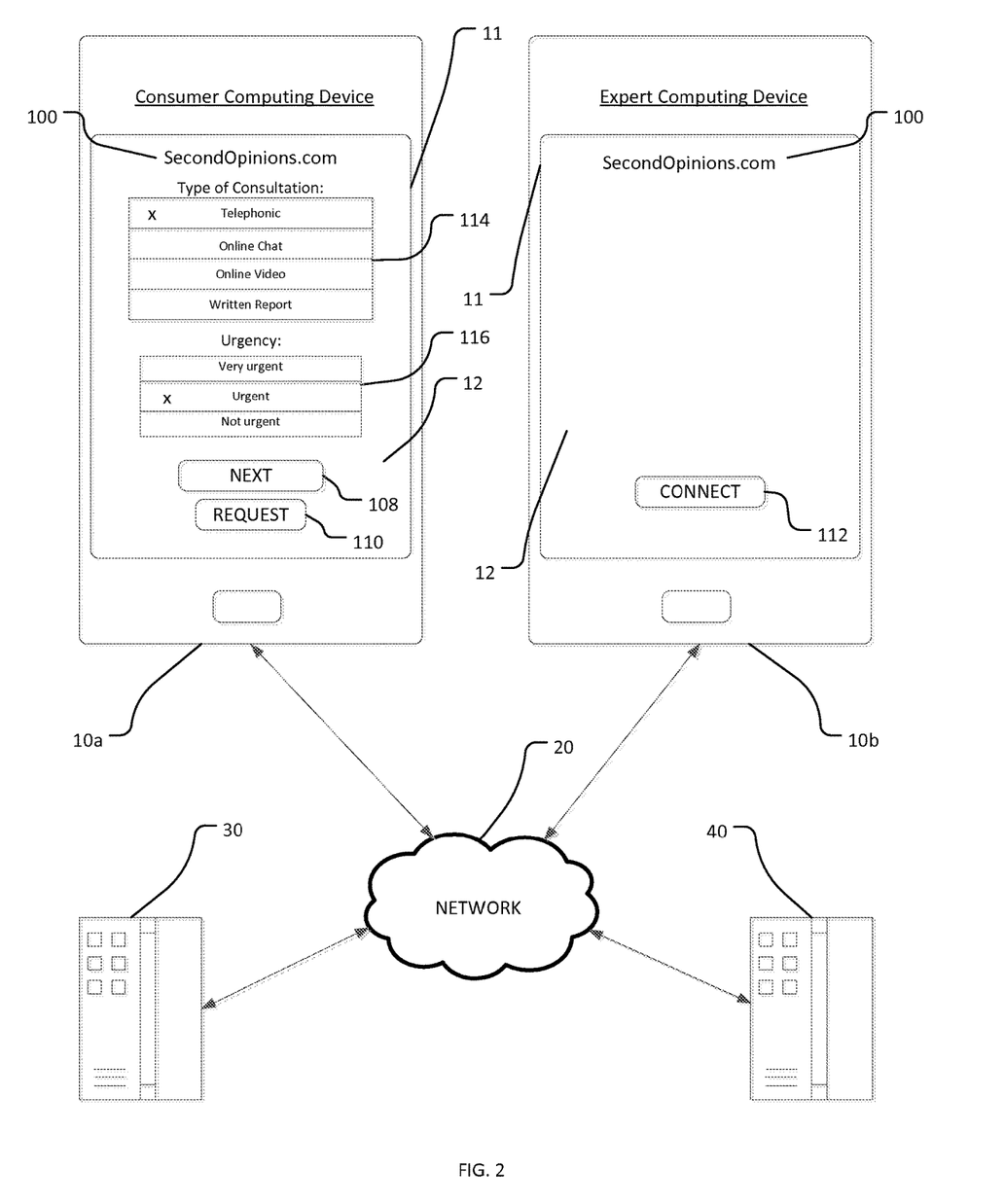
Figure 3:
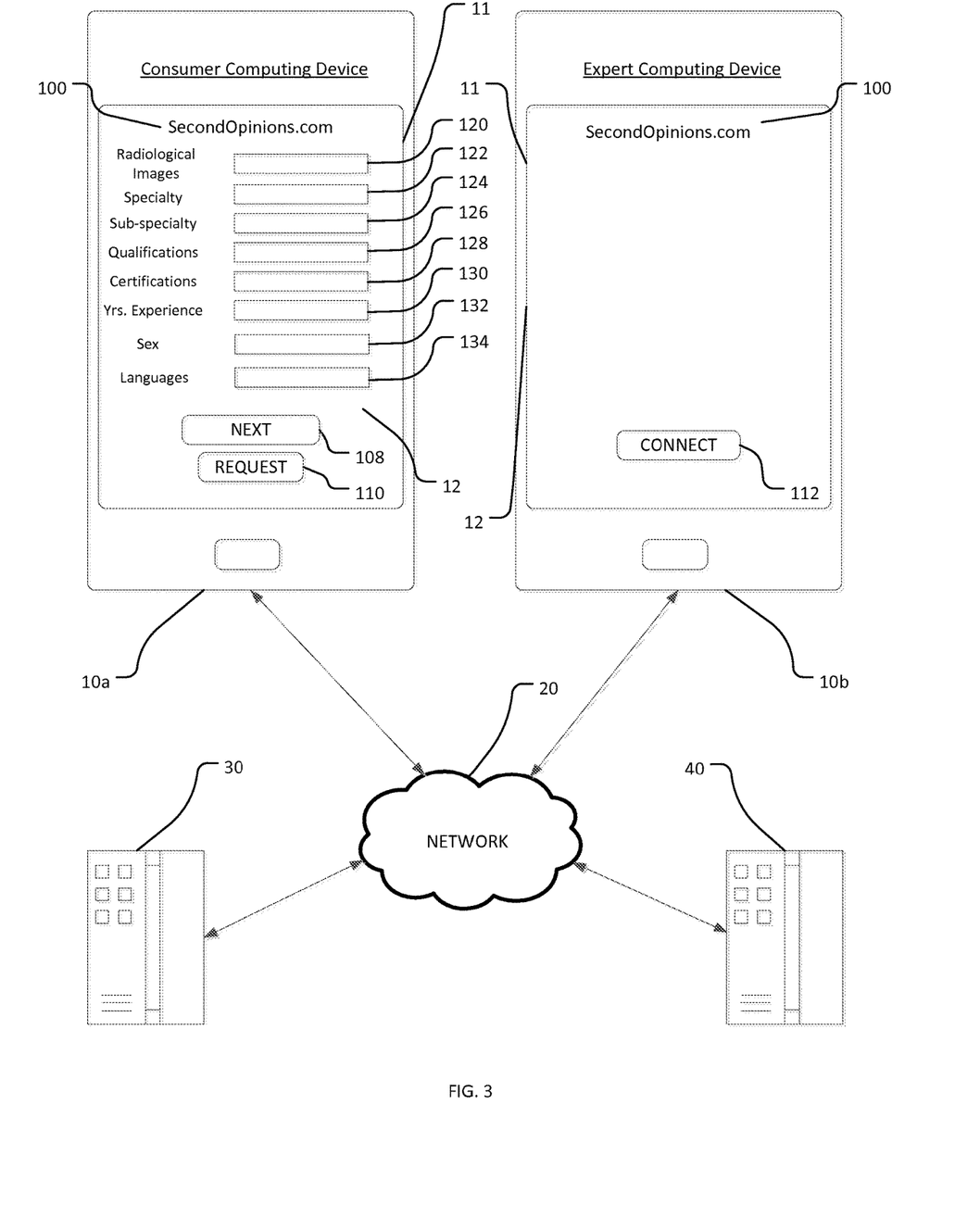

The examples of FIG. 1, FIG. 2 and FIG. 3 are provided for example only and not intended to be limiting. While the consumer input illustrated relates to neurologic radiology, other consumer input related to other subject matter is contemplated and is within the scope of the disclosure. Exemplary subject matter includes legal, insurance, automotive, real estate and business matters.

Figure 4:
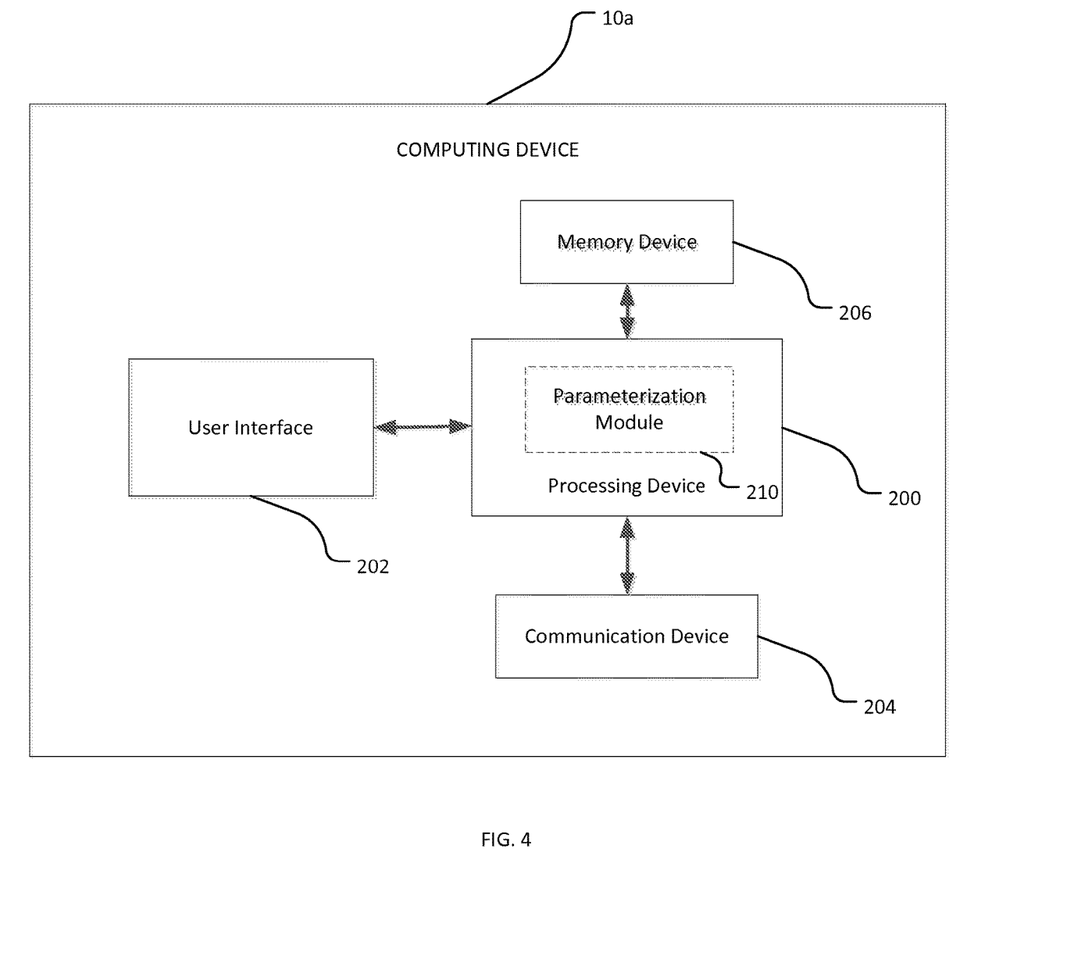
FIG. 4 is a block diagram illustrating components of the computing devices of FIGS. 1-3.

Referring now to FIG. 4, a block diagram illustrating example components of the computing devices 10a and 10b of FIG. 1, FIG. 2 and FIG. 3 is depicted. Since the computing devices 10a and 10b are identical in all structural respects, consumer computing device 10a will be described. In the example embodiment, the consumer computing device 10a includes a processing device 200, a user interface 202, a communication device 204, and a memory device 206.

The processing device 200 can include memory, e.g., read only memory (ROM) and random access memory (RAM), storing processor-executable instructions and one or more processors that execute the processor-executable instructions. In embodiments where the processing device 200 includes two or more processors, the processors can operate in a parallel or distributed manner. The processing device 200 can execute the operating system of the computing device 10a. In the illustrative embodiment, the processing device 200 also executes a parameterization module 210, which is described in greater detail below.

The user interface 202 is a device that allows the consumer to interact with the consumer computing device 10a. While one user interface 202 is shown, the term "user interface" can include, but is not limited to, a touch screen, a physical keyboard, a mouse, a microphone, and/or a speaker. The communication device 204 is a device that allows the consumer computing device 10a to communicate with another device, e.g., the matching server 30, via the network 20. The communication device 204 can include one or more wireless transceivers for performing wireless communication and/or one or more communication ports for performing wired communication. The memory device 206 is a device that stores data generated or received by the computing device 10a. The memory device 206 can include, but is not limited to a hard disc drive, an optical disc drive, and/or a flash memory drive.

In some embodiments, the parameterization module 210 is embodied as processor-executable instructions stored in the memory of the processing device 200. The processing device 200 can execute the parameterization module 210. The parameterization module 210 can be preloaded into the operating system of the computing device 10a, downloaded from the matching server 30, downloaded from a third party server by a consumer of the computing device 10a, or be generated on the consumer computing device 10a.

The parameterization module 210 of the consumer computing device 10a provides the GUI 12 and receives consumer instructions via consumer input. The parameterization module 210 further receives consumer commands to generate a request for an expert second opinion from the matching server 30. The request includes a set of consumer preference parameters generated by the parameterization module 210 from consumer input. The parameterization module 210 generates the set of consumer preference parameters using filtering rules. The parameterization module 210 displays menus and fields on the GUI 12 of the consumer computing device 10a based upon the filtering rules to solicit consumer preferences related to the consumer's request for a second opinion. In some embodiments, the parameterization module 210 assigns weights to the consumer preference parameters based upon weighting rules, including consumer weighting rules, to generate a weighted set of consumer preference parameters Referring now to FIG. 5, a block diagram illustrating an exemplary matching server 30 is depicted. In an exemplary embodiment, the matching server includes a processing device 300, a communication device 302, and a memory device 304.

Figure 5:
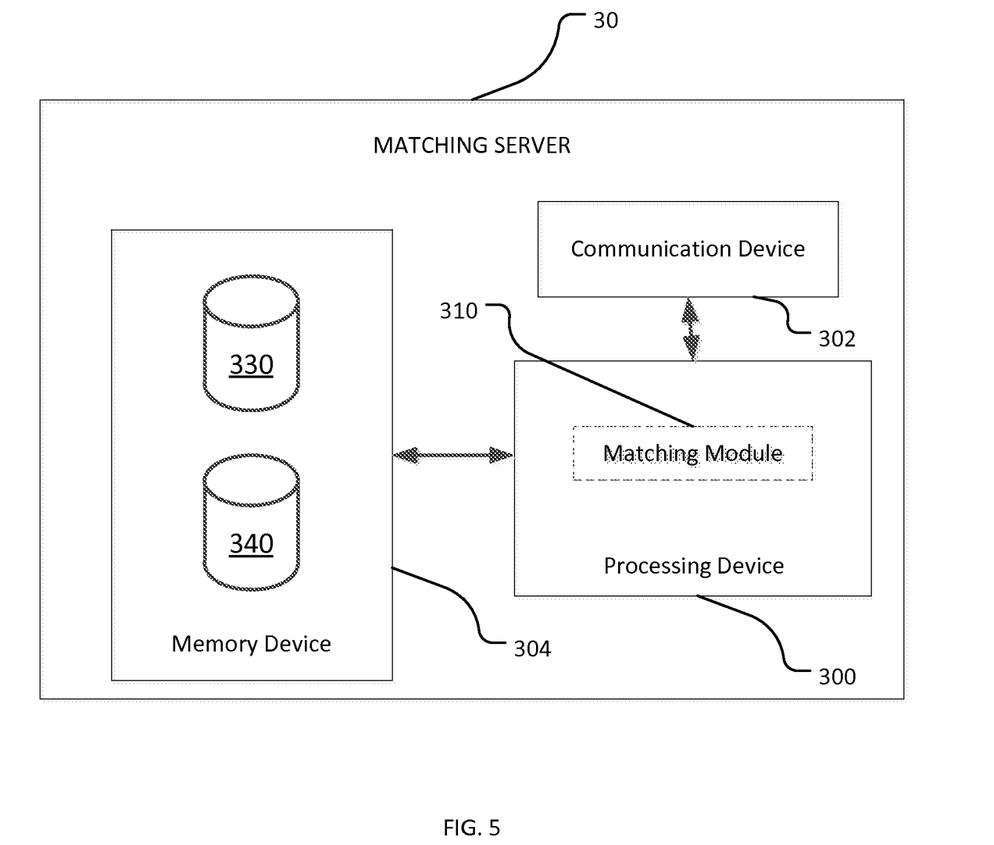
FIG. 5 is block diagram illustrating components of the matching server of FIGS. 1-3.

The processing device 300 can include memory, e.g., read only memory (ROM) and random access memory (RAM), storing processor-executable instructions and one or more processors that execute the processor-executable instructions. In embodiments where the processing device 300 includes two or more processors, the processors can operate in a parallel or distributed manner. In the illustrative embodiment, the processing device 300 executes a matching module 310, which is described in greater detail below.

The communication device 302 is a device that allows the matching server 30 to communicate with another device, e.g., the computing device 10a, via the network 20. The communication device 302 can include one or more wireless transceivers for performing wireless communication and/or one or more communication ports for performing wired communication.

The memory device 304 is a device that stores data generated or received by the matching server 20. The memory device 304 can include, but is not limited to a hard disc drive, an optical disc drive, and/or a flash memory drive. The memory device 304 is accessible to the processing device 300. A participant database 330 and a knowledge database 340, or similar structures, can be stored in the memory device 304.

The participant database 330 stores information related to registered consumers and experts. Information stored in the participant database 330 can include consumer data such as name and address as well as prior requests made by the consumer. Information stored in the participant database 330 can also include parameterized expert data such as name, address, specialty, sub-specialty, current availability, preferred communication method, qualifications, certifications, years of experience, sex, nationality, ethnicity and languages spoken.

The knowledge database 340 stores information relevant to consumer requests. The knowledge database 340 can include text, audio and video files and other relevant files that can be transmitted to the consumer computing device 10*a* by a brokerage server (not shown) such as described in co-pending application Ser. No. 13/773,941. The knowledge database 340 can include artificial intelligence functionality that provides for indexing of records to particular consumer requests.

The matching module 310 receives commands from the consumer computing device 10*a*. The matching module 310 receives a request for an expert second opinion from the consumer computing device 10*a*. As described, the request can include a weighted set of consumer preference parameters. The matching module 310 performs a search of the participant database 330 to determine if there is a match between the consumer's request and a registered expert. The matching module 310 can search the participant database 330 using the consumer preference parameter having the greatest weight or using a combination of weighted consumer preference parameters.

The matching module 310 can send a list of an expert or experts matching the consumer's request to the communication device 302 that in turn transmits the list of experts to the consumer computing device 10*a*. In other embodiments of the present disclosure, the matching module 310 searches the knowledge database 340 and determines if there are any records related to the consumer's request. In some embodiments of the present disclosure, the matching module 310 sends any records related to the consumer's request to the communication device 302 that in turn transmits the records to the consumer computing device 10*a*.

The matching server 30 can be used to provide customer expressed preferences in an automated system for providing radiological second opinions as disclosed in co-pending application Ser. No. 13/662,397. The matching server 30 can also be used to provide matching services in an automated web-based second opinion brokerage system as disclosed in co-pending application Ser. No. 13/773,941. The matching server 30 can further be used to provide matching services in a web-based personalized health management system as disclosed in co-pending application Ser. No. 13/903,898.

Figure 6:
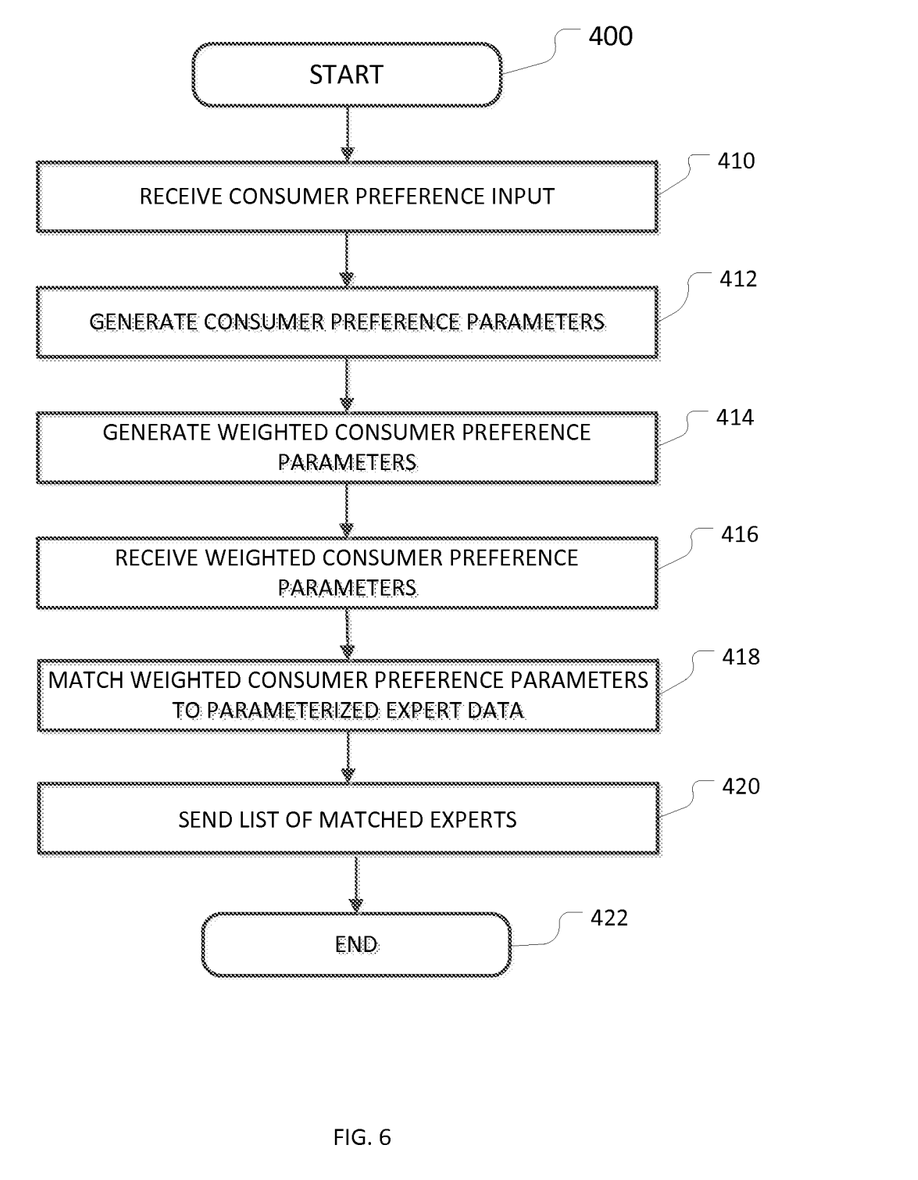
FIG. 6 is a flow chart illustrating an example method for matching a consumer with an expert in accordance with some embodiments of the present disclosure.

Referring now to FIG. 6, an example method 400 for automating the matching of a customer with an expert in a second opinion brokerage system is illustrated. In some embodiments the parameterization module 210 and the matching module 310 execute the method 400. The flowchart and block diagrams in the flow diagrams illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

At operation 410, the parameterization module 210 receives consumer input related to the consumer's request for an expert second opinion. As discussed above, the GUI 12 of the consumer's computing device 10*a* allows the consumer to enter preferences related to the type of second opinion requested as well as the subject matter of the requested second opinion. The parameterization module 210 can apply filtering rules and present the consumer with displays soliciting input related to the type and subject matter of the requested second opinion. At operation 412, the parameterization module 210 can generate a set of consumer preference parameters. At operation 414, the parameterization module 210 can generate a set of weighted consumer preference parameters based upon weighting rules including customer preference weighing rules.

At operation 416, the matching module 310 can receive the set of weighted consumer preference parameters. The matching module 310 can match the set of weighted consumer preference parameters with parameterized expert data at operation 418 to determine a list of one expert or experts that match the consumer's request. At operation 420, the list of matched experts can be sent to the consumer's computing device 10*a*.

The method 400 of FIG. 6 is provided for example and is not intended to be limiting. It should be appreciated that the method 400 can include additional operations and some operations may be varied without departing from the scope of the disclosure.

In one embodiment, the present disclosure utilizes blockchain technology to govern disputes, govern electronic payments between parties, such as, for example, between the consumer and parameterization module 210, and establish communication directly between parties without third-party intermediaries. Blockchains are decentralized, peer-to-peer networked databases that can store and authenticate a ledger of assets and asset transactions. Blockchain technology allows transactions to occur without a third-party intermediary. Blockchain technology uses smart contracts to resolve disputes. Smart contracts are computer programs designed to act as self-executing contracts that implement aspects of a transaction where the terms of the agreement between buyer and seller are directly written into lines of software code. The code and the agreements exist across a distributed, decentralized blockchain network.

The present disclosure allows for transactions to take place across a blockchain database. For example, any electronic payment that is sent by the consumer to, for example, parameterization module 210 following the consumer receiving a list of matched experts can be governed by blockchain technology, specifically using a smart contracts concept, which allows for instantaneous payment.

Further, the present disclosure allows for all radiological second opinions to be stored in a blockchain database.

In another embodiment, processing device 300 can enable matching module 310 to automatically select expert or experts matching the consumer's request to identify an expert or experts to render a second opinion.

In another embodiment, artificial intelligence ("AI") algorithms are used to help experts provide a second opinion.

The above description of illustrated examples of the present invention, including what is described in the Abstract, are not intended to be exhaustive or to be limitation to the precise forms disclosed. While specific embodiments of, and examples for, the invention are described herein for illustrative purposes, various equivalent modifications are possible without departing from the broader spirit and scope of the present invention. Indeed, it is appreciated that the specific example consumer preference parameters are provided for explanation purposes and that other consumer preferences may also be employed in other embodiments and examples in accordance with the teachings of the present disclosure.

I claim:

1. A computer-implemented method for matching a consumer request and an expert able to respond to the request in a second opinion brokerage system comprising the steps of:
    receiving, at a parameterization module of a processing device of a consumer computing device, consumer input indicative of consumer preferences related to the consumer request for a second opinion by an expert, the expert being someone different from a medical practitioner the consumer originally consulted with and who supplied a first opinion, the second opinion from the expert offering a differing point of view from the first opinion, the parameterization module embodied as processor-executable instructions stored in a memory of the processing device;
    determining, by the parameterization module of the consumer computing device, a set of consumer preference parameters by applying parsing and filtering rules to the consumer input;
    implementing, by the parameterization module, weighting rules that assign weights to each of the consumer preference parameters;
    determining, by the parameterization module of the consumer computing device, a weighted set of consumer preference parameters based upon the weighting rules;
    providing, from the parameterization module of the consumer computing device, the set of weighted consumer preference parameters to a processing device of a matching server over a communication network;
    using the weighted set of consumer preference parameters, the matching server,
        queries a database of parameterized expert data including expert characteristics;
        matches the consumer request for a second opinion with at least one expert;
        generates a list of at least one expert that matches the set of weighted consumer preference parameters; and
        provides the list of at least one expert qualified to provide the second opinion, wherein the list of the at least one expert qualified to provide the second opinion is caused to be displayed on a graphical user interface of the consumer computing device; and
    utilizing blockchain technology to govern electronic payments between parties including between the consumer and the parametrization module,
    wherein utilizing blockchain technology comprises:
        creating self-executing smart contracts to implement terms of an agreement between the parties including electronic payments; and
        upon receiving the list of the at least one expert, sending an electronic payment by the consumer to the parametrization module for instantaneous payment.

2. A matching server having a processing device, the matching server comprising:
    a processor configured to:
    (a) receive a set of weighted consumer preference parameters from a consumer computing device, the consumer computing device configured to:
        receive, at a prioritization module of a consumer computing device, consumer input indicative of consumer preferences related to a consumer request for a second opinion by an expert, the expert being someone different from a medical practitioner the consumer originally consulted with and who supplied a first opinion, the second opinion from the expert offering a differing point of view from the first opinion, the prioritization module embodied as processor-executable instructions stored in a memory of a processing device of the consumer computing device;
        determine, by the parameterization module of the consumer computing device, a set of consumer preference parameters by applying parsing and filtering rules to the consumer input;
        implement, by the parameterization module, weighting rules that assign weights to each of the consumer preference parameters; and
        determine, by the prioritization module of the consumer computing device, the weighted set of consumer preference parameters based upon the weighting rules;
    (b) using the weighted set of consumer preference parameters, query a database of parameterized expert data including expert characteristics;
        match the consumer request for a second opinion with at least one second opinion expert; and
        generate a list of at least one expert that matches the set of weighted consumer preference parameters; and
    (c) cause to be displayed on a graphical user interface of the consumer computing device over a communication network, the list of at least one second opinion experts; and
    wherein blockchain technology is used to govern electronic payments between parties including between the consumer and the parametrization module,
    wherein utilizing blockchain technology comprises:
        creating self-executing smart contracts to implement terms of an agreement between the parties including electronic payments; and
        upon receiving the list of the at least one expert, sending an electronic payment by the consumer to the parametrization module for instantaneous payment.

3. The matching server of claim 2, wherein the processor is further configured to use the consumer preference parameter having the greatest weight to query the database.

4. The matching server of claim 2, wherein the processor is further configured to use a subset of the weighted consumer preference parameters to query the database.

* * * * *